United States Patent
Fan et al.

(10) Patent No.: US 6,444,467 B1
(45) Date of Patent: Sep. 3, 2002

(54) **PROCESS FOR PRODUCTION AND SUBSEQUENT *EX VITRO* SOWING AND PROPAGATION OF PRE-GERMINATED PLANT SOMATIC EMBRYOS**

(75) Inventors: Shihe Fan, Vancouver; Daniel Roman Polonenko, Coquitlam; Eric Evert Voogt, Langley; Potter Ann Kathryn Eastman, Vancouver, all of (CA)

(73) Assignee: Cellfor Inc., Brentwood Bay (CA)

( * ) Notice: Subject to any disclaimer, the term of this patent is extended or adjusted under 35 U.S.C. 154(b) by 0 days.

(21) Appl. No.: 09/330,594

(22) Filed: Jun. 11, 1999

Related U.S. Application Data

(60) Provisional application No. 60/089,200, filed on Jun. 12, 1998.

(51) Int. Cl.[7] .............................. C12N 5/00; C12N 5/02
(52) U.S. Cl. .................... 435/430.1; 435/430; 435/420
(58) Field of Search ................................ 435/420, 430, 435/430.1

(56) References Cited

U.S. PATENT DOCUMENTS

| | | | |
|---|---|---|---|
| 4,583,320 A | 4/1986 | Redenbaugh | 47/57.6 |
| 4,777,762 A | 10/1988 | Redenbaugh et al. | 47/57.6 |
| 4,957,866 A | 9/1990 | Gupta et al. | 435/240.4 |
| 5,010,685 A | 4/1991 | Sakamoto et al. | 47/57.6 |
| 5,183,757 A | 2/1993 | Roberts | 435/240.49 |
| 5,183,835 A | 2/1993 | Gross et al. | 523/402 |
| 5,236,469 A | 8/1993 | Carlson et al. | 47/57.6 |
| 5,238,835 A | 8/1993 | McKersie et al. | 435/240.45 |
| 5,294,549 A | 3/1994 | Pullman et al. | 435/240.45 |
| 5,413,930 A | 5/1995 | Becwar et al. | 435/240.49 |
| 5,427,593 A | 6/1995 | Carlson et al. | 47/57.6 |
| 5,451,241 A | 9/1995 | Carlson et al. | 47/57.6 |
| 5,464,769 A | * 11/1995 | Attree et al. | 435/240.4 |
| 5,482,857 A | * 1/1996 | Gupta et al. | 435/240.45 |
| 5,486,218 A | 1/1996 | Carlson et al. | 47/57.6 |
| 5,491,090 A | 2/1996 | Handley, III et al. | 435/240.46 |
| 5,501,972 A | 3/1996 | Westcott | 435/240.49 |
| 5,506,136 A | 4/1996 | Becwar et al. | 435/240.49 |
| 5,563,061 A | * 10/1996 | Gupta | 435/240.45 |
| 5,677,185 A | 10/1997 | Handley, III | 435/422 |
| 5,771,632 A | * 6/1998 | Liu et al. | 47/57.6 |

FOREIGN PATENT DOCUMENTS

| | | | |
|---|---|---|---|
| JP | 2-31624 | * 2/1990 | A01H/4/00 |
| WO | WO 94/24847 | 11/1994 | A01H/4/00 |
| WO | WO 96/37095 | 11/1996 | A01H/4/00 |
| WO | WO 96/37096 | 11/1996 | A01H/4/00 |

OTHER PUBLICATIONS

Fujii et al., Artificial seeds for plant propagation, Trends in Biotechnology, No. 12, vol. 5, pp. 335–339, Dec. 1987.*

Frazier et al., J. Amer. Hort. Sci. 107(4):660–664. 1982.*

Knowles and Dun, Scientia Horticultrae, (1987), 25–33.*

Carlson, W.C. and J.E. Hartle. (1995) Manufactured Seeds of Woody Plants, IN Somatic Embryogenesis of Woody Plants. vol. I. S.M. Jain, P.K. Gupta and R.J. Newton (Eds.) Kluwer Academic Publishers, Dordrecht, The Netherlands. pp. 253–263.

Gupta, P. and J.A. Grob. (1995) Somatic Embryogenesis in Conifers. IN Somatic Embryogenesis of Woody Plants. vol. I. S.M. Jain, P.K. Gupta, and R.J. Newton (Eds.) Kluwer Academic Publishers, Dordrecht, The Netherlands. pp. 81–98.

Lichter, R. (1982) Induction of haploid plants from isolated pollen of *Brassica napus*. Z. Pflanzenphysiol. 105:427–434.

Roberts, D.R., B.S. Flinn, D.T. Webb, F.B. Webster, and B.C.S. Sutton (1990a) Abscisic acid and indole–3–butyric acid regulation of maturation and accumulation of storage proteins in somatic embryos of interior spruce. Physiol. Plant 78:355–360.

Roberts, D.R., B.C.S. Sutton, and B.S. Flinn (1990b) Synchronous and high frequency germination of interior spruce somatic embryos is achieved following partial drying at high relative humidity. Can. J. Bot. 68:1086–1090.

Sakamoto, Y., N. Onishi, and T. Hirosawa. (1995) Delivery Systems for Tissue Culture by Encapsulation. IN Automation and Environmental Control in Plant Tissue Culture. J. Aitken–Christie, T. Kozai, and M.L.A. Smith, Kluwer Academic Publishers, Dordrecht, The Netherlands. pp. 215–243.

Webster, F.B., D.R. Roberts, S.M. McInnis, and B.C.S. Sutton (1990) Propagation of interior spruce by somatic embryogenesis. Can. J. For. Res. 20:1759–1765.

* cited by examiner

*Primary Examiner*—Bruce R. Campell
*Assistant Examiner*—Anne Marie Grunberg

(57) ABSTRACT

A process of producing somatic seedlings from a somatic embryo. The process comprising pre-germinating somatic embryos, placing the pre-germinated somatic embryos into a state of physiological dormancy, sowing the pre-germinated physiologically dormant somatic embryos onto or into germination media, and propagating the sown pre-germinated somatic embryos in environmental conditions manipulated to facilitate imbibition, germination, and development into complete seedlings possessing shoots and roots. Advantageously, the process may be carried out with "naked" embryos (i.e., non-encapsulated or otherwise coated embryos) using conventional seed handling equipment, growing mixes, and plant propagation environments. The process does not require the use of aseptic techniques or sterilized media or equipment. The invention also relates to pre-germinated embryos and seedlings produced by the process.

62 Claims, No Drawings

PROCESS FOR PRODUCTION AND SUBSEQUENT *EX VITRO* SOWING AND PROPAGATION OF PRE-GERMINATED PLANT SOMATIC EMBRYOS

CROSS-REFERENCE TO RELATED APPLICATIONS

This application claims the benefit of U.S. Provisional Application No. 60/089,200, filed Jun. 12, 1998.

BACKGROUND OF THE INVENTION

1. Field of the Invention

This invention relates to methods for propagating plants. More particularly, it relates to methods for handling, sowing, and germinating plant somatic embryos.

2. Description of Related Art

Considerable attention has been given to the development of somatic embryogenesis processes for clonal reproduction of plants and consequently, the specific steps of somatic embryogenesis have been documented in the art for a wide diversity of plant species including both gymnosperms and angiosperms. All methods of somatic embryogenesis are known as tissue culture processes and generally commence with the selection of an explant from a desired plant. The explant is removed from the parent plant tissue by excision and is subsequently cultured on at least one medium to produce a cell mass capable of further differentiation and development. The cell mass can be maintained and proliferated in the undifferentiated state indefinitely, or manipulated to stimulate differentiation into immature somatic embryo structures which can then be cultured further into mature embryos (see, for example, U.S. Pat. Nos. 4,957,866; 5,238,835; 5,294,549; 5,491,090; 5,501,972; 5,563,061; 5,677,185, as well as PCT Publication No. WO 96/37096, all of which are hereby incorporated by reference). Matured somatic embryos can be harvested and germinated immediately, or dried and then germinated, or dried and stored until required for germination (for example, refer to U.S. Pat. Nos. 5,183,835; 5,238,835; 5,413,930; 5,464,769, as well as PCT Publication No. WO 96/37095, all of which are hereby incorporated by reference).

Tissue culture media used to proliferate and propagate plant cultures through the various stages of somatic embryogenesis are typically enriched with mixtures of nutrients that are specifically formulated for each plant species and for the various stages of somatic embryogenesis. A common problem encountered with all somatic embryogenesis processes is microbial, i.e., bacterial, fungal, yeast, contamination of the media and/or plant explants and/or the resulting embryogenic cultures. Microbial contaminants compete with the embryogenic cultures for the nutrients in the media, and in many cases, will infect, consume, parasitize, or otherwise pathogenize the cultures. Consequently, steps must be taken to prevent microbial contamination from the beginning of the embryogenesis process when the tissue explants are excised from the parent tissues, through production, harvesting, drying and germination of the somatic embryos and their subsequent growth into fully functional transplants, i.e., somatic seedlings which can be transplanted into soil or horticultural growing mixes. All manipulations of the cultures at each step of the somatic embryogenesis processes are typically done using aseptic techniques. Embryogenic cultures which show any evidence of microbial contamination at any step in somatic embryogenesis process are sterilized and discarded.

Two of the greatest barriers to commercializing somatic embryogenesis technologies are the processes of sowing and germinating plant somatic embryos. Although numerous protocols are known for the sowing and germination of somatic embryos and growing them into intact functional seedlings, none of these protocols have demonstrated compatibility with conventional horticultural equipment and practices.

Generally, the known protocols for germinating somatic embryos fall into two categories. The first is sowing naked, i.e., uncoated, somatic embryos using aseptic techniques, onto sterilized semi-solid or liquid media contained within a solid-support to facilitate germination (e.g., U.S. Pat. Nos. 5,183,757; 5,294,549; 5,413,930; 5,464,769; 5,506,136) and subsequently, transplanting the germinants into conventional growing systems. The most significant disadvantage of such protocols for sowing naked somatic embryos is that each embryo typically must be handled and manipulated by hand for the germination and transplanting steps. Although various automation options including robotics and machine vision, have been assessed for their usefulness in cost-effective reduction or elimination of the extensive hand-handling currently necessary to sow naked embryos (Roberts et al., 1995), no commercial equipment currently exists which can reliably, aseptically, and cost-effectively perform the in vitro protocols for germination of naked somatic embryos and subsequent transplanting into conventional propagation systems.

The second category of protocols teach encapsulation of somatic embryos (e.g., U.S. Pat. Nos. 4,777,762; 4,957,866; 5,183,757; 5,482,857) to provide a means by which the embryos can presumably be sown with mechanical devices such as seeders and fluidized drills, into conventional growing systems. However, there are a number of disadvantages with gel-encapsulated somatic embryos. For example, the hydrated semi-solid physical characteristics of encapsulated embryos make them incompatible for use with conventional seeding equipment currently available for commercial plant propagation, because the semi-solid gel-encapsulated somatic embryos tend to clump together during handling and consequently, are difficult to singulate and dispense. Furthermore, compositions of encapsulated embryos prepared as taught by the art, clog-up the conventional equipment, and for these reasons, it currently is not possible to sow encapsulated embryos with conventional seeding equipment. Consequently, novel equipment has been developed specifically for delivery of encapsulated somatic embryos into conventional growing systems. Such sowing devices have been reviewed by Sakamoto et al. (1995), but these devices have only been developed and tested as prototypes. Because of mechanical limitations and the high costs associated with the prototype mechanical seeders developed for sowing encapsulated embryos, none are currently available for commercial acquisition and use.

Another disadvantage with encapsulated somatic embryos is the lack of nutrient availability that is characteristically supplied to zygotic embryos by their attendant endosperm or megagametophyte tissues. Consequently, the encapsulation technology for somatic embryos has been extended to include the incorporation of various nutrients such as sugars, fertilizers, oxygen, into the encapsulation medium (e.g., Carlson & Hartle, 1995; U.S. Pat. Nos. 4,583,320; 5,010,685; 5,236,469, all of which are herein incorporated by reference). However, a distinct disadvantage associated with nutrient-amended encapsulated embryos is their susceptibility to microbial invasion during manufacture, storage, and during germination if germinated on non-sterile media.

Furthermore, it must be pointed out that although considerable prior art (e.g., PCT Patent Application WO 94/24847, and U.S. Pat. Nos. 5,010,685; 5,236,469; 5,427,593; 5,427,593; 5,451,241; 5,486,218) teaches methods to manufacture "artificial seeds" consisting of somatic embryos encapsulated in gels, which may or may not be amended with nutrients, and which may or may not be encased within a rigid covering, and although the prior art makes references to sowing said artificial seeds ex vitro into germination media comprised of soil or soilless mixes, the prior art only teaches methods for germinating said artificial seeds in vitro, i.e., on sterilized semi-solid laboratory media. No methods are taught or otherwise disclosed, in the prior art for sowing said encapsulated somatic embryos and/or manufactured and/or artificial seed into conventional growing systems using conventional sowing equipment.

However, the most significant disadvantage with all prior art taught for encapsulating or otherwise coating somatic embryos, is that somatic embryos processed following those protocols typically have, as a consequence, much lower germination vigor and success than corresponding zygotic seeds (Carlson & Hartle, 1995). Carlson and Hartle (1995) concluded that considerable research is still required before "manufactured" or "artificial" seeds based on encapsulation and/or coating of somatic embryos will have practical utility. However, it should be noted that the germination vigor of naked, i.e., uncoated or non-encapsulated somatic embryos produced with methods disclosed in the art can approximate those of the corresponding zygotic seeds (e.g., greater than 85%) (Gupta & Grob, 1995).

BRIEF SUMMARY OF THE INVENTION

An object of the present invention is to facilitate the production of seedlings from somatic plant embryos.

Another object of the invention is to produce pre-germinated somatic embryos of plants that can subsequently or immediately be planted and grown into seedlings.

The present invention relates to a multi-step process to produce seedlings from somatic embryos which begins by germinating somatic embryos and then placing the resultant germinants into dormancy for extended periods of time (e.g. at least 24 hours), for example by drying and/or cooling the embryos, or merely storing them without contact with nutrient solutions. This first component of the multi-step process is referred to as "pre-germination." It has surprisingly been found that pre-germinated embryos placed into a state of physiological dormancy, can be sown and re-germinated when desired or convenient, ex vitro using conventional seeding equipment, into a wide variety of horticultural nursery containers filled with various types of non-sterile growing mixes commonly used in commercial horticultural and agricultural plant propagation.

In one form of the invention, there is provided a process of producing a somatic seedling from a somatic embryo, said process comprising the steps of: pre-germinating a somatic embryo by placing the somatic embryo in contact with a liquid medium used for germinating somatic embryos to produce a pre-germinated somatic embryo, optionally partially immersing the pre-germinated somatic embryo in a solution of abscisic acid (ABA), optionally drying the pre-germinated somatic embryos, placing the pre-germinated somatic embryo on or within the surface of a three-phase substrate, said phases comprising solid, liquid and gas phases, placing said substrate containing said pre-germinated somatic embryo into an environmentally-controlled plant-growing environment, controlling at least one environmental factor in said environment during germination of the pre-germinated somatic embryo to facilitate re-germination, growth and development of the pre-germinated somatic embryo, and applying water and/or nutrient solutions at regular intervals during said period of somatic embryo re-germination to the surface of the substrate in the form of microdroplets such that pre-germinated somatic embryo re-germination, growth and development occur.

Preferably, the somatic embryo is placed in contact with said liquid medium for a period of time in the range of 2–30 days, the medium contains sucrose in a range of 1–9%, the pre-germinated somatic embryo is immersed in said ABA solution for a period of time in the range of ½–2 hours, and the pre-germinated somatic embryo is dried to a moisture content in the range of 5–75%.

The invention, in another aspect, includes a process of producing a pre-germinated somatic embryo, which comprises: pre-germinating a somatic embryo by placing the somatic embryo in contact with a liquid medium used for germinating somatic embryos, optionally partially immersing the pre-germinated somatic embryo in an ABA solution, and optionally drying the pre-germinated somatic embryo. The pre-germinated somatic embryos are preferably placed in a state of physiological dormancy.

The invention also includes a process of producing plant seedlings, which comprises sowing pre-germinated somatic embryos produced by the above process in a three-phase substrate, and growing said pre-germinated somatic embryos. Water and nutrients are preferably applied to a surface of said three-phase substrate in the form of microdroplets, at least to the stage at which the embryos become autotrophic. At this stage, the volume of water or nutrients may be reduced or eliminated altogether.

The invention includes pre-germinated somatic embryos and grown seedlings produced by the above processes.

The process of germinating and then harvesting germinated somatic embryos for re-sowing, is referred to as "pre-germination."

It has also surprisingly been discovered that pre-germinated somatic embryos placed into physiological dormancy, can be desiccated to moisture contents in the range of 5–76%. Furthermore, it has been discovered that desiccated pre-germinated somatic embryos can be stored for extended periods of time without significant declines in physiological integrity or re-germination potential. It has also been discovered that desiccated pre-germinated somatic embryos are amenable for sowing with conventional seeding equipment into conventional plant propagation media for re-germination and further growth and development using conventional plant propagation practices.

Consequently, the preferred multi-step process of the present invention includes, but is not limited to, the steps of pre-germinating somatic embryos, harvesting the pre-germinated embryos, placing the pre-germinated somatic embryos into a state of physiological dormancy, sowing the pre-germinated physiologically dormant somatic embryos onto or into germination media, propagating the sown pre-germinated somatic embryos in environmental conditions manipulated to facilitated imbibition, germination, and development into complete seedlings possessing shoots and roots. Furthermore, the multi-step process may also include, if so desired, a step during which pre-germinated somatic embryos are (a) re-sown immediately after harvesting, or (b) desiccated prior to re-sowing.

An advantage of the present invention, at least in preferred forms, is that it may provide a process by which a somatic embryo can be germinated, harvested from the germination medium, and subsequently sown and re-germinated ex vitro using conventional horticultural and agricultural equipment, containers, growing substrates, and growing environments. Alternatively, after the germinated somatic embryos are harvested, they can be dried and stored for periods of time prior to sowing and re-germination.

Another advantage of the invention, at least in preferred forms, is that it may provide a process by which the germination of somatic embryos followed by harvesting and subsequent ex vitro sowing and re-germination of the germinants, can be practiced with a diverse variety of gymnosperm and angiosperm species. Alternatively, harvested pre-germinated somatic embryos of both gymnosperm and angiosperm species may be desiccated and stored for periods of time prior to ex vitro sowing and re-germination.

There are several additional advantages inherent with the use of the process of the invention, at least in its preferred forms. For example, one advantage of pre-germinating plant somatic embryos is that they generally show exceptional vigor during re-germination and subsequent development into complete seedlings possessing shoots and roots. Furthermore, desiccated pre-germinated somatic embryos are particularly useful for preserving the physiological viability of the embryos during extended storage prior to sowing and re-germination. Yet another advantage of pre-germinating somatic embryos is that they can be sorted according to size, length and shape to facilitate production of more uniform crops after sowing, re-germination and growth.

A key advantage of the present process, at least in preferred forms, is that all components of the multi-step process can be practiced in conventional plant propagation environments without the need for aseptic handling processes for sterile growing environments. More specifically, aseptic procedures, and sterile or sanitized equipment and germination/growing environments are not required for successful germination, desiccation, storage, sowing and re-germination of somatic embryos and their subsequent development into complete functional seedlings, thus enabling the entire pre-germination, sowing and re-germination steps to be performed, if so desired, in commercial plant propagation or greenhouse or nursery growing facilities. However, it is preferable to perform the first step, i.e., germination of somatic embryos, in sterile in vitro conditions.

Another advantage is that the pre-germinated somatic embryos can be sown with conventional seeding equipment such as but not restricted to, vacuum-drum seeders, fluid-drill seeders or needle-jet seeders.

A further advantage is that commonly used horticultural and agricultural products such as, but not restricted to, soil-less seedling mixes or rock wool or foams, can be used as the supports onto which the pre-germinated somatic embryos are sown and subsequently re-germinate into and penetrate with their roots.

Yet a further advantage is that if necessitated by the conditions in the commercial growing environments, existing commercial pesticide products such as, but not restricted to fungicides, bactericides, antibiotics, nematicides, insecticides and the like, which are registered for use with the plant species from which the somatic embryos are produced, can be applied to the sown pre-germinated somatic embryos per label instructions for effective pest control, or alternatively, applied to the growing substrates prior to sowing the somatic embryos.

Another advantage is that exogenous nutrients necessary for successful somatic embryo germination and re-germination can be applied via the various numerous methods, such as misting, fogging, spraying, watering and drenching. Furthermore, the exogenous nutrients can be applied in conjunction with conventional horticultural fertigation practices.

A number of terms are known to have differing meanings when used in literature describing this art. The following definitions are believed to be ones most generally used in the fields of botany, plant somatic embryogenesis, and are consistent with the usage of the terms in the present specification.

"ABA" is abscisic acid, a plant growth regulator.

An "explant" is the organ, tissue or cells derived from a plant and cultured in vitro for the purposes of starting a plant cell or tissue culture.

An "embryogenic culture" is a plant cell or tissue culture capable of forming somatic embryos and regenerating plants via somatic embryogenesis.

"Somatic embryogenesis" is the process of initiation and development of embryos in vitro from somatic cells and tissues.

A "somatic embryo" is an embryo formed in vitro from vegetative (somatic) cells by mitotic division of cells. Early stage somatic embryos are morphologically similar to immature zygotic embryos; a region of embryonal cells subtended by elongated suspensor cells. The embryonal cells develop into the mature somatic embryo.

A "zygotic embryo" is an embryo derived from the sexual fusion of gametic cells.

"Megagametophyte" is haploid nutritive tissue of gymnosperm seed, of maternal origin, within which the gymnosperm zygotic embryos develop.

"Endosperm" is haploid nutritive tissue of angiosperm seed, of maternal origin, within which the angiosperm zygotic embryos develop.

A "clone" when used in the context of plant propagation refers to a collection of individuals having the same genetic constitution, and are produced from a culture that arises from an individual explant.

A "line" is another term for "clone".

"Nutrients" are the inorganic micro- and macro-minerals, vitamins, hormones, organic supplements, and carbohydrates necessary for culture growth and somatic embryo germination.

A "microdroplet" is a self-contained unit of liquid (e.g. water or water-based solution) that is smaller than a drop of the same liquid allowed to form by gravity from a nozzle or solid surface, and is generally contained within a collection of similar microdroplets (e.g. a cloud, mist, fog, fine spray, or the like) produced by applying pressure (e.g. air, a gas or a liquid flowing under pressure provided by a pump) to a drop or other body (e.g. a stream) of the liquid. A microdroplet is usually less than half the size (diameter), and may be less than a quarter or tenth of the size, of a drop of the same liquid, and is preferably small enough to remain temporarily suspended in air (i.e. as an aerosol), and to drift with air currents, rather than fall directly to the ground.

"Autotrophic" refers to the stage of plant development when the photosynthetic organelles and related enzymes and biochemical pathways are fully functional and capable of converting light energy, atmospheric carbon dioxide and water into the pre-requisite carbohydrates (e.g., glucose) necessary to sustain further plant growth and development.

"Physiological dormancy" refers to the cessation of the normal metabolic processes, i.e., anabolism and catabolism, that are inherent in plant growth and development, in a manner that does not negatively affect viability.

"Imbibition" is the absorption and/or adsorption of water by certain colloids present in seeds or embryos, which results in the swelling of the tissues and activation of enzymatic and physiological processes.

"Germination" is a process of development leading to the emergence of a radical or epicotyl or hypocotyl or a root from an embryo and filter development into a complete seedling having shoots and root.

"Pre-germination" is the partial germination of somatic embryos which are harvested and subsequently sown into non-sterile growing media for ex-vitro re-germination, or alternatively, desiccated and stored prior to sowing and re-germination.

DETAILED DESCRIPTION OF THE INVENTION

In a preferred form, the present invention is generally a multi-step process for ex vitro sowing and germination of plant somatic embryos using conventional horticultural equipment and facilities, comprising, but not restricted to, some or all of the following sequential steps:

1. Sowing the plant somatic embryos onto physical supports placed within containers which contain a liquid germination medium, said embryos placed onto the physical supports in a manner such that the embryos are not submerged in the liquid medium, but instead, such that the liquid medium forms a thin capillary layer around the embryo, said capillary layer also referred to as a film.
2. Incubating the somatic embryos surrounded with a film of germination medium for a period of time ranging between 2–30 days such that embryo germination commences as evidenced by the emergence of a shoot and a root.
3. Placing the containers with the somatic germinants into cold storage, said cold storage comprised of temperatures in range of 2–15° C., preferably in the range of 4–10° C., for at least, but not limited to, 1 day.
4. Conditioning the somatic germinants by transferring them from the containers containing germination medium to containers containing an ABA solution in the range of 2–100 $\mu$M, preferably in the range of 5–20 $\mu$M, for a period of time ranging between 30–180 minutes, preferably in the range of 60–90 minutes.
5. Drying the conditioned germinants by transferring them from the containers containing the ABA solution, to a drying chamber, said drying chamber maintaining a relative atmospheric humidity in the range of 35–99% RH, preferably in the range of 80–99%, and incubating said conditioned germinants in said drying chamber for a period of time ranging between 12 hours to 7 days, preferably in the range of 18 hrs to 48 hrs.
6. Storing said conditioned and dried embryos in a sealed package in a facility wherein the temperature is maintained in the range of −85° to 30° C., preferably in the range of 2–20° C.
7. Sowing the pre-germinated plant somatic embryos into nursery containers containing a three-phase substrate, said three phases comprising solids, liquids and air.
8. Placing the nursery containers sown with plant somatic embryos, into a conventional plant propagation environment in which light, temperature, atmospheric humidity, and moisture content of the rooting substrate can be controlled and manipulated to enable and facilitate the re-germination of the somatic embryos and their further development into seedlings.
9. Supplying an aerosol to the surface of the nursery containers sown with somatic embryos, said aerosol containing the necessary carbohydrate compounds required to initiate and sustain the re-germination processes of the somatic embryos.
10. Supplying in the forms of an aerosol and/or a liquid suspension and/or a liquid solution, the micro- and macro-mineral elements required to sustain the re-germination of somatic embryos and their subsequent development into seedlings.
11. Adjusting as required during the somatic embryo re-germination period, the ambient light intensity and diurnal photoperiod, temperature and atmospheric humidity to maintain the development of re-germinated somatic embryos into fully functional seedlings.

Alternatively, at the completion of step 2, pre-germinated embryos may be sown directly after harvesting, i.e., per steps 7–11.

A particular advantage of the process, at least in its preferred forms, is that special hygienic and/or aseptic and/or sterile handling methods and/or equipment and/or facilities are not required to successfully handle, sow and germinate, dry, and re-germinate plant somatic embryos. Accordingly, these steps may be carried out in non-sterile, unhygienic and/or septic conditions, preferably using "naked" embryos (i.e., non-encapsulated or otherwise coated embryos).

It is preferable that the invention be practiced with plant somatic embryos that have been dried to moisture contents that approximate those of their corresponding zygotic seeds, i.e., in the range of 5–20% and more specifically, in the range of 10–15%. However, it is possible to practice the present invention with somatic embryos containing higher moisture contents in the range of 20–70% with the only limitation on the upper limit being the highest level of moisture content that the somatic embryos can be singulated with conventional seeding or seed-handling equipment.

It is preferable that the pre-germination step is carried out in a container wherein there is a physical support such as, but not restricted to, filter paper or a screen comprised of a nylon or polypropylene material or other such materials, is placed on the liquid germination medium such that plant somatic embryos are held on the surface or above the surface of the liquid medium such that a thin capillary layer or film of the germination medium is formed around the somatic embryos. Alternatively, the somatic embryos can be successfully pre-germinated on discontinuous physical substrates comprised of materials such as but not limited to, vermiculite, perlite, peat, coconut husk fibres and the like, said discontinuous supports containing sufficient liquid germination medium to enable the formation of a thin capillary layer or film of germination medium around the somatic embryos. The somatic embryos can be sown onto the surface of the absorbent material by hand or by the means of a mechanical sowing device such as but not restricted to conventional seeding equipment.

However, it is also possible to accomplish the pre-germination of somatic embryos by sowing them with conventional seeding equipment into empty multi-chambered nursery containers exemplified by but not restricted to miniplug trays, said containers having their drainage holes covered by a mesh-like material which will support the somatic embryos after sowing. The containers are then placed onto liquid germination media such that the somatic embryos are in contact with but are not submerged in the liquid media, such that a thin layer of film of germination medium is formed around the somatic embryos.

Although the pre-germinated and subsequently dried somatic germinants can be sown with all conventional seeding equipment used for sowing zygotic seeds, it is preferred to use equipment that dispenses singulated seed into multi-chambered nursery containers, commonly referred to as miniplug trays or cell-packs, said containers commonly used to produce plant plugs which can be mechanically transplanted into larger containers or into field-growing environments.

Another important advantage of the present invention, at least in its preferred forms, is that the sowing and propagation of pre-germinated somatic embryos can be practiced with a wide variety of non-sterilized growing substrates commonly used in conventional plant propagation. The preferred growing substrate is peat-based and has been formulated specifically for germination of zygotic seed and is exemplified by mixtures such as (a) 15.2 cu.ft of peat, 8 cu.ft. of vermiculite, 680 grams of dolomite lime, and 300 grams of Micromax® (a commercial fertilizer composition comprised of microelements such as but not limited to sulfur, boron, manganese, magnesium, cobalt and iron), and (b) 16.2 cu.ft. of peat, 6.75 cu.ft. perlite, 4 cu.ft. vermiculite, 6 kilograms of dolomite lime, 1.5 kilograms of gypsum, 375 grams of potassium phosphate, 250 grams Micromax®, and 35 grams of wetting agent. Alternatively, commercially formulated mixes such as PRO-MIX-G® or PRO-MIX-PGX® (Premier Peat Moss Ltd. Montreal, PQ, Canada—these are commercial soilless plant growing media comprised of mixtures containing but not limited to peat, perlite, vermiculite and pumice), Sunshine Mix #3 (Sun-Gro Horticulture Inc., Hubbard, Oreg., USA), and Redi-Earth® (The Scotts Co., Marysville, Ohio, USA—this is a commercial soilless plant growing media comprised of mixtures containing but not limited to peat, perlite, vermiculite and pumice) can also be used with the present invention. It is preferred that the peat-based growing substrate is moistened to a moisture content in the range of 59–75% and then dispensed into multi-chambered trays commonly used for production of plant plugs. Although examples of such trays include Styrofoam #252 miniplug trays manufactured by Beaver Plastics Inc (Edmonton, AB, Canada) and hard plastic #288 or #512 miniplug trays manufactured by TLC Polyform Inc (Plymouth Minn., USA, 55441), the present invention can be practiced with other such multi-chambered trays, or alternatively, with individual pots. It should be noted that the practice of the present invention is not restricted to peat-based mixtures, but also includes other substrate such as Jiffy-7 peat plugs, composted or shredded coconut husk fibres commonly referred to as "cor" or "coir" (1993 Crystal Co., St. Louis, Mo., USA), polymerized substrates (Grow Tech Inc., San Juan Bautista, Calif. USA; Preforma Inc., Oberlin, Ohio USA), extruded foams such as Oasis( (Smithers-Oasis Ltd., Kent, Ohio, USA—this is a commercial expanded foam product comprised of urea formaldehyde), rock wool (Rockwool International A/S, Hovedgaden 584, DK-2640, Denmark) and the like. Regardless of the rooting substrate chosen, it's physical characteristics should enable development and maintenance of a high relative humidity in the gaseous phase, i.e., in excess of 75% RH, within the substrate while minimizing saturation of the substrate with the liquid phase.

After the pre-germinated somatic embryos are sown onto the surfaces of the rooting substrates, if desired, the embryos may be covered with a thin layer of additional rooting substrate that may be comprised of the same material underneath the embryos or alternatively, with a different type of material. One non-limiting example is sowing the pre-germinated embryos onto PRO-MIX-PGX medium, then overlaying the embryos with a thin layer of coconut husk fibres.

Nursery containers sown with pre-germinated somatic embryos are preferentially placed into a conventional plant propagation environment wherein the conditions are within but not limited to the ranges of temperatures of 15–35° C., relative humidities of 75–100%, light intensities of 10–500 foot candles, and diurnal cycles of 6 h day/18 h night–22 h day/2 h night.

It is preferable to maintain a very high level of atmospheric humidity around the nursery containers sown with pre-germinated somatic embryos, i.e., greater than 90% RH, for the first 3–7 days after sowing to facilitate somatic embryo imbibition and germination. A number of methods can be used to maintain the atmospheric humidity at these levels including but not restricted to placing the containers in a greenhouse environment with misting or fogging equipment which is deployed at controlled intervals, placing the containers in a fogging or misting tent or chamber, placing clear plastic domes over the nursery containers and then removing domes periodically to mist or fog the sown embryos and replacing the domes immediately thereafter. Another non-limiting method is to provide a space ranging between 2 mm and 10 mm above the surface of the rooting substrate onto which the embryos are sown and the top of the container, and then covering the top of the nursery container with a plastic film which is removed to enable misting or fogging of the sown embryos and then immediately replaced. After somatic embryo germination is established as evidenced by development of epicotyl and root structures, the germinants can be weaned from the high relative humidity environments and integrated into conventional nursery cultural practices by gradually reducing the amount of misting/fogging applied and/or by extending the periods of time between the misting or fogging steps.

It is preferable to maintain the sown pre-germinated embryos in a high relative humidity environment, i.e., greater than 90% RH, for a period of, but not restricted to, 3–7 days after sowing to facilitate embryo imbibition, prior to supplying exogenous nutrients required for embryo germination.

Another important feature of the invention, at least in preferred forms, is that the exogenous nutrients, including but not restricted to carbohydrates and minerals, required for successful somatic embryo re-germination and subsequent growth and development may be applied as aerosols. The nutrient solutions may be applied with, but not restricted to, conventional misting and/or fogging equipment. Although, the nutrients can be applied individually or combined into one solution, it is preferred to supply the carbohydrates as one solution and the remaining nutrients as a separate solution. A non-limiting example of how this can be practiced is by applying a 3% sucrose solution as a mist to the surface of the growing substrate containing a sown pre-germinated embryo, and then applying at a later time, a solution containing a mixture of mineral nutrients formulated to deliver 454 mg/l nitrogen, 81 mg/l phosphorus, 704 mg/l potassium, 50 mg/l calcium, 39 mg/l magnesium, 193 mg/l sulfur, 3 mg/l manganese, 0.5 mg/l zinc, 89 mg/l chlorine, 3 mg/l iron, 0.7 mg/l iodine, 0.6 mg/l boron, 0.01 mg/l molybdenum, 0.01 mg/l cobalt, and 0.01 mg/l copper. Alternatively, the macronutrients can be supplied as a commercial formulation such as but not restricted to PlantProd® Plant Starter Fertilizer 10-52-10 (nitrogen-phosphatepotassium) or PlantProd® Forestry Seedling Starter 11-41-8 (nitrogen-phosphate-potassium) (Plant Products Ltd., Brampton, ON, Canada—these are commercial water-soluble fertilizers containing mineral nutrients such as nitrogen, phosphorus and potassium, and a dye).

An alternative non-limited means of supplying exogenous nutrients to pre-germinated somatic embryos sown onto three-phase growing media within nursery containers is to irrigate or "drench" the media with nutrient solutions formulated as previously described. This is preferably done just before the embryos are sown in the three-phase growing media.

Since microorganisms such as fungi, bacteria, yeast, and algae, are ubiquitous in conventional plant propagation substrates, equipment, containers and growing environments, a wide variety of chemical and biological pesticide products are available to control and eradicate plant pathogens. It has surprisingly been found that aseptic handling procedures and sterilized growing substrates, nursery containers and environments are not required to successfully germinate and grow plant somatic embryos. Indeed, the invention can be practiced in conventional plant propagation environments using only the standard commercial methods of hygiene. Furthermore, we have surprisingly found that pesticides such as Benlate® (a commercial fungicide composition containing a chemical active ingredient), Rovril® (a commercial fungicide composition containing a chemical active ingredient), Trumpet® (a commercial insecticide composition containing a chemical active ingredient) and the like, which are registered for pest control in plant crops, can be used in conjunction with somatic embryos pre-germinated and subsequently sown with the present novel multi-step procedure.

The following Examples are provided to further illustrate the present invention and are not to be construed as limiting the invention in any manner.

EXAMPLE 1

Somatic embryos of interior spruce (*Picea glauca* (Moench) Voss x *P. engelmannii* Parry ex Engelm.) lines I-1026, and 10-1418 were produced and dried with a high-relative-humidity treatment (HRHT) according to the methods of Roberts et al. (1990a; 1990b) and Webster et al. (1990).

Two groups of dried embryos for each of the two genotypes, were germinated on Whatman #1 filter paper on a thin layer of cotton in polycarbonate boxes. The liquid germination medium was modified GMD medium ($NH_4^+$—N/$NO_3^-$—N ratio was 1.4; phosphate concentration was 6 mM; 3% sucrose). After the embryos were sown onto the filter paper, the liquid level in the germination boxes was adjusted to provide a liquid film surrounding the surface of embryos situated at the interface with the solid support. The boxes were sealed with Parafilm and placed in a controlled environment room with the temperature maintained at a constant 23° C.

The first group of somatic embryos was germinated for 7 days after which, the polycarbonate boxes containing the germinants were transferred into refrigerated storage (i.e., temperatures were within a range of 8–12° C.) for 72 hours. The germinants were then removed from the cold treatment and subsequently received the various ABA treatments described below. The germinants which received the cold treatment are hereafter referred to as "stored germinants".

The second group of somatic embryos did not receive a cold treatment but instead, received a 10-day germination period. This group of germinants is referred to hereafter as "fresh germinants".

The stored and fresh germinants of each genotype were carefully paired into four groups, on wetted paper towel disks in separate 10 cm Petri dishes and received four ABA treatments, said ABA treatments being concentrations of 0, 5, 10, 20 µM, respectively. The ABA treatments were applied in darkness for 90 min.

After the completion of the ABA treatments, the somatic germinants were blot-dried on paper towels. The germinants were then transferred to fresh 5 cm Petri dish. The dishes, two per drying chamber, were placed in drying chambers containing a saturated KCl solution, which provided an atmospheric humidity of 85% RH over the liquid surface in a sealed chamber at 20° C. The somatic germinants were dried for 24 hr in a refrigerated room maintained between 5–8° C. after which, the drying chambers were transferred into a controlled environment room maintained at 20° C. for another 15 h.

After the HRHT treatment was completed, 3 samples of 3 germinants were taken from each germinant type of each genotype in each ABA treatment, for determination of their Relative Water Contents (RWC).

The dried germinants were sown into 288-cavity miniplug trays (TLC Polyform Inc,. Plymouth Minn., USA, 55441) filled with a peat-based soilless mix comprised of 60% peat and 40% coarse horticultural vermiculite. Each germinant type of each genotype in each ABA treatment was randomly sown into 5 minitrays in blocks of 20 germinants. After sowing, the germinants were covered with a thin layer of coir (1993 Crystal Co., St. Louis, Mo., USA). The trays were wrapped in black plastic bags for 18 hrs to allow slow rehydration of germinants. Then, the trays were misted with a modified GMD nutrient solution (Webster et al., 1990) containing 3% sucrose until the soilless mix and coir became well wetted. The trays were placed in two misting chambers in a controlled environment germination room under light reduced by a 50% shade cloth for the first week. The shade cloth was removed at the end of the first week and the germinants were exposed to a light intensity of 180 µmol $m^{-2}s^{-1}$ photosynthetic photon flux. The chambers were frequently misted to keep the soilless mix moistened. Modified GMD solution with 3% sucrose was sprayed onto the germinants daily. After 7 days, germinants were fertilized weekly with 20-20-20 fertilizer (Plant Products Ltd., Brampton, ON, Canada) to deliver the equivalent of 100 ppm N.

The effects of the cold storage and ABA treatments on re-germination of desiccated, pre-germinated spruce somatic embryos are summarized in Table 1.

TABLE 1

Effects of in vitro pre-germination, cold storage and ABA treatments on ex vitro re-germination of spruce somatic embryos.

| Genotype | Post-germination Treatment | ABA treatment | Relative water content (%) | Re-germination success (%) |
|---|---|---|---|---|
| I-1026 | "fresh" | 0 | 54.7% | 48.8% |
| | | 5 | 54.4% | 35.0% |
| | | 10 | 33.4% | 53.3% |
| | | 20 | 25.8% | 48.2% |
| | "stored" | 0 | 81.2% | 65.8% |

TABLE 1-continued

Effects of in vitro pre-germination, cold storage and ABA treatments on ex vitro re-germination of spruce somatic embryos.

| Genotype | Post-germination Treatment | ABA treatment | Relative water content (%) | Re-germination success (%) |
|---|---|---|---|---|
|  |  | 5 | 85.2% | 71.8% |
|  |  | 10 | 79.3% | 74.3% |
|  |  | 20 | 87.6% | 73.5 |
| 10-1418 | "fresh" | 0 | 19.6% | 10.0% |
|  |  | 5 | 29.5% | 53.8% |
|  |  | 10 | 23.4% | 16.6% |
|  |  | 20 | 54.1% | 29.8% |
|  | "stored" | 0 | 54.1% | 51.1% |
|  |  | 5 | 60.2% | 59.8% |
|  |  | 10 | 71.3% | 57.5% |
|  |  | 20 | 76.8% | 60.0% |

These data demonstrate that spruce somatic embryos can be successfully germinated in vitro, stored, and subsequently, re-germinated ex vitro in non-sterile soilless mixes.

EXAMPLE 2

Somatic embroyos of interior spruce (*Picea glauca* (Moench) Voss x *P. engelmannii* Parry ex Engelm.) lines 1-1278, 4-2809, 107-1917, 143-2695, and I-1026 were produced and dried with a high-relative-humidity treatment (HRHT) according to the methods of Roberts et al. (1990a; 1990b) and Webster et al. (1990). The embryos were then incubated in a liquid nutrient solution containing 3% sucrose for 3 days, then germinated for 4 days in polycarbonate boxes (Sigma-Aldrich Canada Ltd., 2149 Winston Park Dr., Oakville, Ont., Canada; catalog #C8062). The sterile pre-germination substrate in each box consisted of 150 ml of coarse vermiculite plus 150 ml of modified GMD nutrient solution amended with 3% sucrose (Roberts et al., 1990b; Webster, 1990). The 4-day-old pregerminated somatic embryos were harvested from the vermiculite, then hand-sown into soilless mixes composing of 50% screened peat and 50% fine perlite in TLC Polyform 288-cell miniplug trays (10 ml/cavity). After showings were completed, the trays were placed in a humidified growth chamber for 1 week under the following environmental conditions: 95–98% RH, day/night air temperatures of 25/20° C., an 18 h light/6 h dark diurnal period, and light intensity of 30 $\mu$mol m$^{-2}$s$^{-1}$ photosynthetic photon flux. A modified nutrient germination liquid medium containing 3% sucrose was sprayed onto the trays once every weekday. The trays were then moved to misting chambers with similar environmental conditions except light intensities were increased to 120–150 $\mu$mol m$^{-2}$s$^{-1}$ photosynthetic photon flux. The misting frequencies were 4 seconds at 2.5 h intervals during the day and 2 seconds at 3 h intervals at night. The trays were sprayed with a modified nutrient germination liquid medium containing 3% sucrose once every weekday for one additional week. Thereafter, a 0.5 g/l PlantProd® Forestry Starter Fertilizer solution (N-P-K; 11-41-8) was applied twice weekly. The re-germination successes of the different lines of pre-germinated interior spruce SE were assessed at different time periods ranging between 2–11 weeks after sowing. The results are summarized in Table 2.

TABLE 2

Ex vitro re-germination performance of pre-germinated interior spruce SE lines in a non-sterile soilless growing mix.

| Interior spruce line # | Time period after ex vitro sowing | Re-germination success (%) |
|---|---|---|
| 1-1278 | 3 weeks | 100% |
| 4-2809 | 8 weeks | 61% |
| 107-1917 | 11 weeks | 59% |
| 143-2695 | 2 weeks | 100% |
| I-1026 | 4 weeks | 100% |

These data demonstrate that interior spruce SE can be germinated, harvested and then successfully re-germinated ex vitro when sown in a non-sterile soilless growing mix.

EXAMPLE 3

Somatic embryos (SE) of interior spruce line 1-1281 were produced according to the methods of Roberts et al. (1990a; 1990b) and Webster et al. (1990). After harvesting, the SE were dried using the HRHT method. Post-HRHT embryos were germinated on Whatman #1 filter paper placed on a thin layer of cotton in polycarbonate boxes. The liquid germination medium was modified GMD medium ($NH_4^+$—N/$NO_3^-$—N ratio was 1.4; phosphate concentration was 6 mM; 3% sucrose). After the embryos were sown onto the filter paper, the liquid level in the germination boxes was adjusted to provide a liquid film surrounding the surface of embryos situated at the interface with the solid support. The boxes were sealed with Parafilm and placed in a controlled environment room with the temperature maintained at a constant 23° C. After a 7-day in vitro germination period, the polycarbonate boxes containing the germinants were transferred to cold storage (8– 10° C.) for 56 hours. The germinants were then transferred to clean petri dishes and were incubated in a 10 $\mu$mol ABA solution for 1.5 h after which, they were blot-dried on paper towels.

The germinants were separated into 7 groups and then randomly assigned to 1 of 7 desiccation treatments (the RH values were: 75.8%; 81.9%; 84.6%; 86.3%; 88.7%; 92.6%; 96.7%). The germinants were desiccated for 48 h at 5° C. After the desiccation treatments were completed, sub-samples of the germinated, then desiccated spruce somatic embryos (i.e., pre-germinated embryos), were taken for determination of their water contents.

The dried germinants were sown into 252-cavity miniplug trays (Beaver Plastics Ltd., Edmonton, AB, Canada) filled with a peat-based soilless mix comprised of 60% peat and 40% coarse horticultural vermiculite (lightly pre-moistened with a dilute fertilizer solution, 20-20-20, 100 ppm N equivalent). Four replicates of 20 germinants per .treatment were randomly assigned to four miniplug trays. After sowing, the germinants were covered with a thin layer of coir (1993 Crystal Co., St. Louis, Mo., USA). The trays were wrapped in black plastic bags overnight to allow slow rehydration of the desiccated germinants. The next day, the trays were sprayed with a ½ strength GMD solution containing 3% sucrose (Roberts et al., 1990b), until the soilless mix and the coir became well moistened. The trays were then placed into a misting chamber under a light intensity of 30 $\mu$mol m$^{-2}$s$^{-1}$ for the first week, 55 $\mu$mol m$^{-2}$s$^{-1}$ for the second week and 165 $\mu$mol m$^{-2}$s$^{-1}$ for the remainder of the experiment. The light levels were adjusted by placing shading cloth underneath the lighting bulb. The chamber was misted 3 sec per hour for the day and 2 second per 2 hours for the night. A modified GMD solution containing 3% sucrose was sprayed onto the germinants once every day on weekdays for the first three weeks.

The effects of the different desiccation treatments on re-germination of pre-germinated, then desiccated somatic embryos from spruce line 1-1281 are summarized in Table 3.

TABLE 3

Effects of various desiccation treatments on the survival and ex vitro re-germination of interior spruce line 1-1281 pre-germinated somatic embryos.

| Desiccation | Pre-germinated spruce somatic embryos | |
|---|---|---|
| Treatment (% RH) | Moisture content (%) | Re-germination success (%) |
| 75.8% | 63.6% | 3.8% |
| 81.9% | 75.1% | 39.5% |
| 84.6% | 76.4% | 47.6% |
| 86.3% | 79.9% | 45.0% |
| 88.7% | 83.4% | 69.0% |
| 92.6% | 85.4% | 60.0% |
| 96.7% | 87.1% | 77.5% |

These data demonstrate that somatic embryos of spruce can be germinated in vitro, desiccated and then successfully re-germinated ex vitro in non-sterile peat-based growing substrate.

EXAMPLE 4

Somatic embryos (SE) of interior spruce (*Picea glauca engelmannii* complex) line 1-1281 were produced according to the methods of Roberts et al. (1990a; 1990b) and Webster et al. (1990). After harvesting, the SE were dried using the HRHT method. Post-HRHT embryos were germinated in sterile conditions on Whatman #1 filter paper placed on a thin layer of cotton in polycarbonate boxes. The liquid germination medium was modified GMD medium ($NH_4^+$—$N/NO_3^-$—N ratio was 1.4; phosphate concentration was 6 mM; 3% sucrose). After the embryos were sown onto the filter paper, the liquid level in the germination boxes was adjusted to provide a liquid film surrounding the surface of embryos situated at the interface with the solid support. The boxes were sealed with Parafilm and placed in a controlled environment room with the temperature maintained at a constant 23° C. After a 10-day in vitro germination period, the polycarbonate boxes containing the germinants were transferred to cold storage (8–10° C.) for 30 hours. The germinants were then transferred to clean petri dishes and were incubated in a 10 $\mu$mol ABA solution for 75 min after which, they were blot-dried on paper towels.

The germinants were separated into 7 groups and then randomly assigned to 1 of 9 desiccation treatments (Group A: 75.7%; 81.5%; 84.2% RH at 5° C.; Group B: 84.2%, 86.0%; 88.5% RH at 12° C.; Group C: 88.5%, 92.4%; 96.7% RH at 20° C.). The germinants were desiccated for 48 h. After the desiccation treatments were completed, subsamples of the germinated, then desiccated spruce somatic embryos (i.e., pre-germinated embryos), were taken for determination of their water contents.

The dried germinants were sown into 252-cavity miniplug trays (Beaver Plastics Ltd., Edmonton, AB, Canada) filled with a peat-based soilless mix comprised of 60% peat and 40% coarse vermiculite (lightly pre-moistened with a dilute fertilizer solution, 20-20-20, 100 ppm N equivalent). Four replicates of 20 germinants per treatment were randomly assigned to four miniplug trays. After sowing, the germinants were covered with a thin layer of coir (1993 Crystal Co., St. Louis, Mo., USA). The trays were wrapped in black plastic bags overnight to allow slow rehydration of the desiccated germinants. The next day, the trays were sprayed with a modified GMD solution containing 3% sucrose (Roberts et al., 1990b), until the soilless mix and the coir became well moistened. The trays were then placed into a misting chamber under a light intensity of 30 $\mu$mol m$^{-2}$s$^{-1}$ for the first week, 55 $\mu$mol m$^{-2}$s$^{-1}$ for the second week and 165 $\mu$mol m$^{-2}$s$^{-1}$ for the remainder of the experiment. The light levels were adjusted by placing shading cloth underneath the lighting bulb. The chamber was misted 3 sec per hour for the day and 2 second per 2 hours for the night. A modified GMD solution containing 3% sucrose was sprayed onto the germinants once every day on weekdays for the first three weeks. The effects of the different desiccation treatments on the survival and re-germination of pre-germinated somatic embryos from spruce line 1–1281 were determined after 4 weeks, and are summarized in Table 4.

TABLE 4

Effects of various desiccation treatments and temperatures on the survival and ex vitro re-germination of interior spruce line 1-1281 pre-germinated somatic embryos.

| | | Desiccated pre-germinated spruce embryos | |
|---|---|---|---|
| Desiccation temperature (° C.) | Desiccation treatment (% RH) | Relative water content (%) | Re-germination success (%) |
| 5° C. | 75.8% | 48.8% | 35.0% |
| 5° C. | 81.9% | 75.9% | 68.3% |
| 5° C. | 84.6% | 74.1% | 55.0% |
| 12° C. | 84.6% | 77.9% | 43.3% |
| 12° C. | 86.2% | 75.1% | 61.7% |
| 12° C. | 88.6% | 80.6% | 78.3% |
| 20° C. | 88.6% | 37.0% | 21.1% |
| 20° C. | 92.4% | 67.1% | 51.7% |
| 20° C. | 96.7% | 99.3% | 73.3% |

These data demonstrate that somatic embryos of spruce can be germinated in vitro, desiccated and then successfully re-germinated ex vitro in non-sterile peat-based growing substrate.

EXAMPLE 5

Post-HRHT treatment somatic embryos of *Pinus taeda* line C-3419 were germinated for 7 days in sterile conditions on Whatman #1 filter paper placed onto a thin layer of cotton in polycarbonate boxes. The liquid germination medium was modified GMD medium ($NH_4^+$—$N/NO_3^-$—N ratio was 1.4; phosphate concentration was 6 mM; 3% sucrose). After the embryos were sown onto the filter paper, the liquid level in the germination boxes was adjusted to provide a liquid film surrounding the surface of embryos situated at the interface with the solid support. The boxes were sealed with Parafilm and placed in a controlled environment room with the temperature maintained at a constant 23° C. After a 7-day in vitro germination period, the polycarbonate boxes containing the germinants were transferred to cold storage (8–10° C.) for 48 hours. The germinants were then transferred to clean petri dishes and were incubated in a 10 $\mu$mol ABA solution for 1.5 h after which, they were blot-dried on paper towels.

The germinants were separated into 7 groups and then randomly assigned to 1 of 7 desiccation treatments (the RH values were: 75.8%; 81.9%; 84.6%; 86.3%; 88.7%; 92.6%; 96.7%). The germinants were desiccated for 48 h at 5° C. After the desiccation treatments were completed, subsamples of the germinated, then desiccated *Pinus taeda* somatic embryos (i.e., pre-germinated embryos), were taken for determination of their water contents.

The dried germinants were sown into 252-cavity miniplug trays (Beaver Plastics Ltd., Edmonton, AB, Canada) filled with a peat-based soilless mix comprised of 60% peat and 40% coarse horticultural vermiculite (lightly pre-moistened with a dilute fertilizer solution, 20-20-20, 100 ppm N equivalent). Four replicates of 20 germinants per treatment were randomly assigned to four miniplug trays. After sowing, the germinants were covered with a thin layer of coir (1993 Crystal Co., St. Louis, Mo., USA). The trays were wrapped in black plastic bags overnight to allow slow rehydration of the desiccated germinants. The next day, the trays were sprayed with a modified GMD solution containing 3% sucrose (Roberts et al., 1990b), until the soilless mix and the coir became well moistened. The trays were then placed into a misting chamber under a light intensity of 30 $\mu$mol m$^{-2}$s$^{-1}$ for the first week, 55 $\mu$mol m$^{-2}$s$^{-1}$ for the second week and 165 $\mu$mol m$^{-2}$s$^{-1}$ for the remainder of the experiment. The light levels were adjusted by placing shading cloth underneath the lighting bulb. The chamber was misted 3 sec per hour for the day and 2 second per 2 hours for the night. A ½ strength GMD solution containing 3% sucrose was sprayed onto the germinants once every day on weekdays for the first three weeks.

Effects of the different desiccation treatments on survival and re-germination of pre-germinated somatic embryos from *Pinus taeda* line C-3419 are summarized in Table 5.

TABLE 5

Effects of various desiccation treatments on the survival and ex vitro re-germination of *Pinus taeda* line C-3419 pre-germinated somatic embryos.

| Desiccation Treatment (% RH) | Pre-germinated *Pinus taeda* somatic embryos | |
|---|---|---|
| | Moisture content (%) | Re-germination success (%) |
| 75.8% | 51.7% | 0% |
| 81.9% | 61.6% | 5.0% |
| 84.6% | 74.9% | 20.0% |
| 86.3% | 74.6% | 15.0% |
| 88.7% | 78.4% | 38.9% |
| 92.6% | 82.7% | 49.7% |
| 96.7% | 85.0% | 61.6% |

These data demonstrate that somatic embryos of *Pinus taeda* can be germinated in vitro, desiccated and then successfully re-germinated ex vitro in non-sterile peat-based growing substrate if the pre-germinated SE are not overly desiccated.

EXAMPLE 6

Somatic embryos of *Pinus radiata* lines Pr-6552 and Pr-6804 were pre-germinated in vitro for 23 days in polycarbonate boxes (Sigma-Aldrich Canada Ltd., 2149 Winston Park Dr., Oakville, Ont., Canada; catalog #C8062). The sterile pre-germination substrate in each box consisted of 150 ml of coarse vermiculite plus 150 ml of modified GMD nutrient solution amended with 3% sucrose (Roberts et al., 1990b; Webster, 1990).

After the pre-germination period was completed, the germinants were sorted into 7 groups with each group placed into a separate petri dish. The 7 groups of germinants were then simultaneously incubated for 1 h in 10 $\mu$m ABA solutions. After the ABA treatment was completed, each group of germinants was surface-dried by blotting with paper towels.

Then, each group of germinants was randomly assigned to 1 of 7 desiccation treatments (the RH values were: 75.8%; 81.9%; 84.6%; 86.3%; 88.7%; 92.6%; 96.7%). The germinants were desiccated for 48 hours in a refrigerated environment (5°–8° C.). After the desiccation treatments were completed, subsamples of the germinated, then desiccated *Pinus radiata* somatic embryos (i.e., pre-germinated embryos), were taken for determination of their water contents. Their "relative water contents" were calculated using the mean water content of 5 blotted samples after ABA treatment as the saturated base line.

The desiccated pre-germinated *Pinus radiata* somatic embryos were sown into 288-cell miniplug flats manufactured by TLC Polyform Inc (Plymouth Minn., USA, 55441). The soilless growing media used was comprised of 1:1 mixture of screened peat and fine perlite. After sowing was completed, the flats were placed into a high-humidity growth chamber (+85% RH) for 4 weeks and then moved into a misting chamber for 8 additional weeks. The germinants were fertilized weekly with an 11-41-8 (N-P-K) forestry starter fertilizer solution (Plant Products Ltd., Brampton, ON, Canada) over the 12-week re-germination period. The effects of the different desiccation treatments on the survival and re-germination of pre-germinated *Pinus radiata* somatic embryos are summarized in Table 6.

TABLE 6

Effects of desiccation treatments on the survival and ex vitro re-germination of pre-germinated *Pinus radiata* somatic embryos.

| Desiccation Treatment (% RH) | *Pinus radiata* line Pr-6552 | | *Pinus radiata* line Pr-6804 | |
|---|---|---|---|---|
| | Relative water content (%) | Re-germination success (%) | Relative water content (%) | Re-germination success (%) |
| 75.8% | 18% | 58% | 18% | 41% |
| 81.9% | 53% | 88% | 43% | 76% |
| 84.6% | 50% | 90% | 49% | 67% |
| 86.3% | 64% | 69% | 58% | 85% |
| 88.7% | 85% | 67% | 72% | 79% |
| 92.6% | 80% | 92% | 70% | 75% |
| 96.7% | 61% | 78% | 56% | 68% |

These data demonstrate that *Pinus radiata* somatic embryos can be germinated for a period of time, then desiccated and subsequently re-germinated. Furthermore, these data indicate that the re-germination of desiccated pre-germinated *Pinus radiata* somatic embryos can be accomplished ex vitro in non-sterile soilless mixes commonly used in conventional horticulture practice.

EXAMPLE 7

Matured canola (*Brassica napus* L.) somatic embryos were harvested and conditioned in NLN-13 liquid medium (Lichter, 1982) for one week as follows. Embryos were placed in 250-ml baffled Erlenmeyer flasks containing 100 ml of medium. The flasks were then placed onto a shaker (60 rpm) under constant (24 h/day) illumination at 20–30 $\mu$mol m$^{-2}$s$^{-1}$ of photosynthetic photon flux. The conditioned embryos were then germinated in vitro for a period of 7 days at 23° C., in polycarbonate boxes (Sigma-Aldrich Canada Ltd., 2149 Winston Park Dr., Oakville, Ont., Canada; catalog #C8062) containing 150 ml of coarse vermiculite and 150 of a liquid germination medium amended with 3% sucrose. After the 7-day pre-germination period, the boxes containing the germinated canola somatic embryos were given a 3-day "cold treatment" at 5° C.

After the pre-germination period was completed, the germinants were sorted into 7 groups with each group placed into a separate petri dish. The 7 groups of germinants were then simultaneously incubated for 1 h in 10 μm ABA solutions. After the ABA treatment was completed, each group of germinants was surface-dried by blotting with paper towels.

Then, each group of germinants was randomly assigned to 1 of 7 desiccation treatments (the RH values were: 75.8%; 81.9%; 84.6%; 86.3%; 88.7%; 92.6%; 96.7%). The germinants were desiccated for 4 days at 23° C. After the desiccation treatments were completed, subsamples of the germinated, then desiccated canola somatic embryos (i.e., pre-germinated embryos), were taken for determination of their water contents.

The desiccated pre-germinated canola somatic embryos were sown into 288-cell miniplug flats. The soilless growing media used was comprised of 3:2 mixture of screened peat and fine perlite. After sowing was completed, the flats were placed into a misting chamber for 3 weeks. The germinants were fertilized weekly with an 11-41-8 (N-P-K) forestry starter fertilizer solution (Plant Products Ltd., Brampton, ON, Canada). The effects of the different desiccation treatments on the survival and re-germination of pre-germinated canola somatic embryos are summarized in Table 7.

TABLE 7

Effects of desiccation treatments on the survival and ex vitro re-germination of pre-germinated Brassica napus somatic embryos.

| Desiccation | Pre-germinated canola somatic embryos | |
|---|---|---|
| Treatment (% RH) | Relative water content (%) | Re-germination success (%) |
| 75.7% | 10% | 0% |
| 81.5% | 23% | 34% |
| 84.2% | 32% | 76% |
| 86.0% | 43% | 68% |
| 88.5% | 81% | 67% |
| 92.6% | 69% | 84% |
| 96.7% | 85% | 95% |

These data demonstrate that that somatic embryos from an angiosperm species, Brassica napus, can be germinated for a period of time, then desiccated and subsequently re-germinated. Furthermore, these data indicate that the re-germination of desiccated pre-germinated Brassica napus somatic embryos can be accomplished ex vitro in non-sterile soilless mixes commonly used in conventional horticulture practice.

REFERENCES MENTIONED IN THE APPLICATION

1. Carlson, W. C. and J. E. Hartle. (1995) Manufactured Seeds of Woody Plants. IN Somatic Embryogenesis of Woody Plants. Vol. I. S. M. Jain, P. K. Gupta, and R. J. Newton (Eds.) Kluwer Academic Publishers, Dordrecht, The Netherlands. pp. 253–263.
2. Gupta, P. and J. A. Grob. (1995) Somatic Embryogenesis in Conifers. IN Somatic Embryogenesis of Woody Plants. Vol. I. S. M. Jain, P. K. Gupta, and R. J. Newton (Eds.) Kluwer Academic Publishers, Dordrecht, The Netherlands. pp. 81–98.
3. Lichter, R. (1982) Induction of haploid plants from isolated pollen of Brassica napus. Z. Pflanzenphysiol. 105:427–434.
4. Roberts, D. R., B. S. Flinn, D. T. Webb, F. B. Webster, and B. C. S. Sutton (1990a) Abscisic acid and indole-3-butyric acid regulation of maturation and accumulation of storage proteins in somatic embryos of interior spruce. Physiol. Plant 78:355–360.
5. Roberts, D. R., B. C. S. Sutton, and B. S. Flinn (1990b) Synchronous and high frequency germination of interior spruce somatic embryos is achieved following partial drying at high relative humidity. Can. J. Bot. 68:1086–1090.
6. Sakamoto, Y., N. Onishi, and T. Hirosawa. (1995) Delivery Systems for Tissue Culture by Encapsulation. IN Automation and Environmental Control in Plant Tissue Culture. J. Aitken-Christie, T. Kozai, and M. L. A. Smith, Kluwer Academic Publishers, Dordrecht, The Netherlands. pp. 215–243.
7. Webster, F. B., D. R. Roberts, S. M. McInnis, and B. C. S. Sutton (1990) Propagation of interior spruce by somatic embryogenesis. Can. J. For. Res. 20:1759–1765.

What is claimed is:

1. A process of producing a somatic seedling from a somatic plant embryo, said process comprising the steps of:
   (a) pre-germinating a somatic embryo by placing the somatic embryo in contact with a liquid medium used for germinating somatic embryos to produce a pre-germinated somatic embryo,
   (b) optionally contacting the partially germinated somatic embryo with a solution of abscisic acid (ABA),
   (c) drying the pre-germinated somatic embryo,
   (d) placing the dried pre-germinated somatic embryo on or within the surface of a non-sterile three-phase substrate, said phases comprising solid, liquid and gas phases,
   (e) placing said substrate containing said dried pre-germinated somatic embryo into an environmentally-controlled plant-growing environment,
   (f) controlling at least one environmental factor in said environment during germination of the dried pre-germinated somatic embryo to facilitate ex vitro re-germination, growth and development of the dried pre-germinated somatic embryo into a normal somatic seedling possessing shoot and root, and
   (g) applying water and/or nutrient solutions at regular intervals during said period of somatic embryo re-germination to the surface of the substrate in the form of microdroplets or by irrigating or drenching the three-phase substrate such that said ex vitro re-germination, growth and development of said dried pre-germinated somatic embryo occur to produce said normal somatic seedling possessing shoot and root.

2. The process of claim 1 wherein said somatic embryo is placed in contact with said liquid medium for a period of time in the range of 2–30 days and then harvested.

3. The process of claim 2 wherein said liquid medium contains sucrose in a range of 1–9%.

4. The process of claim 1 wherein the pre-germinated somatic embryo is at least partially immersed in said ABA solution for a period of time in the range of ½–2 hours.

5. The process of claim 4 wherein said ABA solution contains 5–100 μM of ABA.

6. The process of claim 1 wherein said pre-germinated somatic embryo is dried in step (c) to a moisture content in the range of 5–75%.

7. The process of claim 1 wherein said at least one environmental factor is selected from the group comprised of a moisture level within said three-phase substrate, atmospheric humidity, temperature, nutrients, light intensity, and diurnal photoperiod.

8. The process of claim 7 wherein the moisture level within the three-phase substrate is maintained in the range of 60–85% during the period of pre-germinated somatic embryo imbibition and germination.

9. The process of claim 7 wherein the atmospheric humidity within the plant growing environment is maintained in the range of 75–100% during the period of pre-germinated somatic embryo germination.

10. The process of claim 9 wherein the atmospheric humidity is maintained by the addition of water in the form of microdroplets delivered through a process selected from a group of processes comprising misting, fogging, and humidification.

11. The process of claim 7 wherein the temperature within the plant growing environment is maintained in the range of 15–37° C.

12. The process of claim 1 wherein said nutrient solutions are applied at intervals ranging between 1 minute–24 hours for a period of 2–8 weeks.

13. The process of claim 1 wherein the somatic embryo is from an angiosperm species.

14. The process of claim 1 wherein the somatic embryo is from a gymnosperm species.

15. The process of claim 1 wherein the pre-germinated somatic embryo is stored for a period of time prior to placing the pre-germinated somatic embryo into a three-phase substrate for germination, growth and development.

16. The process of claim 15 wherein the pre-germinated somatic embryo is stored frozen.

17. The process of claim 15 wherein the pre-germinated somatic embryo is stored under refrigeration at a temperature within the range of 0° C.–ambient.

18. The process of claim 15 wherein the pre-germinated somatic embryo is stored at ambient temperatures.

19. The process of claim 1 wherein the solid phase of the three-phase substrate is selected from the group consisting of peat, sawdust, bark chips, wood chips, compost, moss, perlite, vermiculite, pumice, grit, sand, soil, cellulosic fibres of plant origin, extruded foams, extruded fibres, and chemically expanded foams.

20. The process of claim 1 wherein the three-phase substrate contains a wetting agent.

21. The process of claim 1 wherein the three-phase substrate is sterilized prior to receiving a pre-germinated somatic embryo.

22. The process of claim 1 wherein the moisture content of the three-phase substrate is adjusted with water to a range of 60–85% prior to receiving a pre-germinated somatic embryo.

23. The process of claim 1 wherein the moisture content of the three-phase substrate is adjusted with a nutrient solution to a range of 60–85% prior to receiving a pre-germinated somatic embryo.

24. The process of claim 1 wherein at least one fungicide to control plant pathogens is incorporated into the three-phase growth substrate.

25. The process of claim 1 wherein at least one fungicide to control plant pathogens is applied in liquid form to the three-phase substrate.

26. The process of claim 1 wherein at least one fungicide to control plant pathogens is applied in aerosol form to the three-phase substrate.

27. The process of claim 1 wherein at least one insecticide to control plant pests is incorporated into the three-phase growth substrate.

28. The process of claim 1 wherein at least one insecticide to control plant pests is applied in liquid form to the three-phase substrate.

29. The process of claim 1 wherein at least one insecticide to control plant pests is applied in aerosol form to the three-phase substrate.

30. The process of claim 1 wherein the three-phase substrate is contained within a horticultural container.

31. The process of claim 30 wherein the horticultural container is a tray containing cells.

32. The process of claim 31 wherein the horticultural tray is a miniplug tray.

33. The process of claim 30 wherein the horticultural container is a pot.

34. The process of claim 1 wherein said pre-germinated somatic embryo placed on or within the three-phase substrate, is covered with a material selected from the group consisting of peat, sawdust, bark chips, wood chips, compost, moss, perlite, vermiculite, pumice, grit, sand, soil, cellulosic fibres of plant origin, extruded foams, extruded fibres, and chemically expanded foams.

35. The process of claim 1 wherein said pre-germinated somatic embryo is placed on or within the three-phase substrate with seeding equipment.

36. The process of claim 35 wherein the seeding equipment is a vacuum drum seeder.

37. The process of claim 35 wherein the seeding equipment is a needle jet seeder.

38. The process of claim 35 wherein the seeding equipment is a fluid drill seeder.

39. The process of claim 1 wherein the nutrients applied to the surface of the three-phase substrate containing the pre-germinated somatic embryo, are delivered through a process selected from the group consisting of misting, fogging, and humidification.

40. The process of claim 1 wherein the nutrients applied to the surface of the three-phase substrate are selected from the group consisting of sugars, inorganic minerals, micronutrients, amino acids, vitamins, and plant growth regulators.

41. The process of claim 40 wherein the sugars are selected from the group consisting of monosaccharides and polysaccharides.

42. The process of claim 40 wherein the sugars are selected from the group consisting of glucose, fructose, mannose, maltose, and sucrose.

43. The process of claim 1 wherein only water is applied as microdroplets to the surface of the three-phase substrate for a period of 18–36 hours after placing a pre-germinated somatic embryo on or within the surface of the three-phase substrate, after which time, nutrient solutions are also applied as microdroplets.

44. The process of claim 1 wherein said somatic embryo is placed in contact with said liquid media for a period of time in the range of 2–30 days.

45. The process of claim 1 wherein said media of step (a) contains sucrose in the range of 1–5%.

46. The process of claim 1 wherein said pre-germinated somatic embryo is partially immersed in step (b) for a period of 1–2 hours.

47. The process of claim 1 wherein said ABA concentration of the solution in step (b) is 10–20 $\mu$mol.

48. The process of claim 1 wherein said pre-germinated somatic embryo is dried in step (c) to a moisture content of 5–75%.

49. The process of claim 1 wherein said at least one environmental factor in said environment is controlled according to the following steps:
  (a) maintaining the moisture level within the three-phase substrate in the range of 60–85% during the period of pre-germinated somatic embryo germination into the substrate,
  (b) maintaining the atmospheric humidity within the plant growing environment in the range of 75–100% during the period of pre-germinated somatic embryo germination into the substrate, and
  (c) maintaining the temperature within the plant growing environment in the range of 15–37° C.

50. The process of claim 49 wherein the moisture content of the three-phase substrate is maintained in the range of 65–75%.

51. The process of claim 49 wherein the atmospheric humidity within the plant-growing environment is maintained in the range of 85–95%.

52. The process of claim 49 wherein the temperature within the plant-growing environment is maintained in the range of 20–30° C.

53. A process of producing a dried pre-germinated somatic embryo, which comprises:
  (a) pre-germinating a somatic embryo by placing the somatic embryo in contact with a liquid medium used for germinating somatic embryos,
  (b) optionally partially immersing the pre-germinated somatic embryo in an ABA solution, and
  (c) drying the pre-germinated somatic embryo.

54. The process of claim 53 wherein said pre-germinated somatic embryos are placed in a state of physiological dormancy.

55. A process of producing plant seedlings, which comprises sowing pre-germinated somatic embryos produced by the process of claim 53 in a three-phase substrate, and growing said pre-germinated somatic embryos.

56. The process of claim 55 wherein water and nutrients are applied to a surface of said three-phase substrate in the form of microdroplets.

57. The process of claim 56 wherein said water and nutrients are applied as said microdroplets at in a volume prior to a stage in which the embryos become autotrophic, and then said nutrients are applied in a smaller volume after said embryos become autotrophic.

58. The process of claim 57 wherein said embryos become autotrophic after a period of time from sowing in the range of 3–8 weeks.

59. The process of claim 56, wherein the application of water and nutrients to the surface of the three-phase substrate in the form of microdroplets is terminated when the germinated somatic embryos become autotrophic.

60. A process of producing a dormant pre-germinated somatic embryo which comprises: pre-germinating a somatic embryo by contacting the embryo with a liquid medium used for germinating somatic embryos, and placing said pre-germinated somatic embryo into a state of physiological dormancy by drying said pre-germinated somatic embryo.

61. The process of claim 60 wherein the pre-germinated somatic embryos are dried to a moisture content in the range of 5–75%.

62. A process of producing somatic seedlings from somatic embryos, said process comprising pre-germinating somatic embryos, placing said pre-germinated somatic embryos into a state of physiological dormancy by drying said embryos, sowing said dried pre-germinated physiologically dormant somatic embryos onto or into germination media, and propagating said sown dried pre-germinated somatic embryos in ex vitro environmental conditions manipulated to facilitate imbibation, germination, and development into complete normal seedlings possessing shoots and roots.

* * * * *